(12) United States Patent
Dixon et al.

(10) Patent No.: US 7,478,014 B2
(45) Date of Patent: Jan. 13, 2009

(54) METHOD AND SYSTEM FOR FACILITATING PREVENTIVE MAINTENANCE OF AN OPTICAL INSPECTION TOOL

(75) Inventors: David Dixon, Austin, TX (US); Michael Kincaid, Kyle, TX (US)

(73) Assignee: Tokyo Electron Limited, Tokyo (JP)

( * ) Notice: Subject to any disclaimer, the term of this patent is extended or adjusted under 35 U.S.C. 154(b) by 73 days.

(21) Appl. No.: 11/529,352

(22) Filed: Sep. 29, 2006

(65) Prior Publication Data
US 2008/0082283 A1  Apr. 3, 2008

(51) Int. Cl.
G06F 19/00 (2006.01)
(52) U.S. Cl. .................................................. 702/184
(58) Field of Classification Search .................. 702/184
See application file for complete search history.

(56) References Cited

U.S. PATENT DOCUMENTS

| | | | |
|---|---|---|---|
| 5,338,630 A * | 8/1994 | Yoon et al. ................. | 430/30 |
| 6,722,798 B2 | 4/2004 | Senba et al. | |
| 6,811,962 B2 | 11/2004 | Yoshihara et al. | |
| 6,991,385 B2 | 1/2006 | Yoshihara et al. | |
| 2005/0146716 A1 | 7/2005 | Dixon et al. | |
| 2006/0055908 A1 * | 3/2006 | Urban et al. ................. | 355/69 |

OTHER PUBLICATIONS

Alan Carlson, et al, "Correlation of Wafer Backside Defects to Photolithography Hot Spots Using Advanced Macro Inspection", Presented at 31st International Symposium, Microlithography - An SPIE Event, Feb. 2006, 7 pgs.

* cited by examiner

Primary Examiner—Tung S Lau
(74) Attorney, Agent, or Firm—Oblon, Spivak, McClelland, Maier & Neustadt, P.C.

(57) ABSTRACT

A method of determining preventive maintenance for an optical inspection system for inspecting photolithography processed substrates. The method includes measuring at least one operational characteristic of the optical inspection system and comparing a measurement result for said at least one operational characteristic with predetermined preventive maintenance criteria for the operational characteristic. Also included is determining a preventive maintenance requirement based on a comparison result of said comparing, and initiating a preventive maintenance action on said optical inspection system, said preventive maintenance action corresponding to said preventive maintenance requirement. A method of automatically performing preventive maintenance on an optical inspection system, and for retrofitting an optical inspection system to facilitate preventive maintenance of the optical inspection system are also disclosed.

12 Claims, 7 Drawing Sheets

| MAINTENANCE ACTION | NUMBER STROBES | TOTAL VOLTAGE | SIGNATURE |
|---|---|---|---|
| LAMP CALIBRATION | 100,000 | Voltage 1 | Image 1 |
| LAMP REPLACEMENT | 20,000,000 | Voltage 2 | Image 2 |
| DETECTOR CALIBRATION | 140,000 | Voltage 3 | Image 3 |

FIG. 3

METHOD AND SYSTEM FOR FACILITATING PREVENTIVE MAINTENANCE OF AN OPTICAL INSPECTION TOOL

BACKGROUND OF THE INVENTION

1. Field of the Invention

The disclosed invention relates generally to an optical inspection system used for inspecting substrates after photolithography processing, and more specifically to facilitating preventive maintenance of such an optical inspection system.

2. Discussion of the Background

In a manufacturing process of a semiconductor device, a prescribed circuit pattern is formed on the surface of a semiconductor wafer by photolithography. In the photolithography step, a series of treatments are carried out such that a resist film is formed on a cleaned semiconductor wafer by supplying a photoresist solution onto the semiconductor wafer, exposing the resist film to light in a prescribed pattern and subsequently developing the pattern.

Although the chance of misprocessing at any single lithography step is small, a typical wafer goes through 20 to 25 lithography steps. Excursions due to process equipment problems, mishandling, and contamination can occur at each of these steps, so the cumulative probability of a wafer experiencing a yield-limiting defect becomes significant. While some defects impact only a small area of the wafer and may not require rework, other defects impact 30% or more of the wafer. These are defined as global defects. After develop inspection (ADI) procedures detect, classify, and disposition wafers with lithography defects for rework. Typical defects include problems with photo resist or ARC/BARC coating, edge bead processing, exposure, alignment, and development, as well as defects caused by contamination or handling, such as particles or scratches. Each recovered wafer can result in savings of thousands, or even tens of thousands of dollars, in revenue.

Many of economically re-workable defects are macroscale, and thus manually detectable through visual inspection by trained operators at microscope stations. Since manual inspection is a relatively slow process compared to the photolithography process throughput, automatic inspection has recently been performed by an after develop inspection (ADI) system to improve throughput.—Further, ADI systems can inspect 100% of wafers processed and can detect defects down to 50 μm.

In typical photolithography systems, after various coating, expose, and develop steps, the wafers are delivered to an ADI inspection station that captures a series of whole wafer images using simultaneous dark and bright field illumination. A full-color image of 100% of the wafer is captured and is characterized by its RGB signature. Such a signature has three elements: a red value, a green value, and a blue value that vary within a predetermined range such as 0-255. The resulting image or signature is compared to that of a "golden" wafer with no defect and a confidence score is assigned indicating how similar the signatures are. When a significant difference is detected, further analysis is performed, to classify the defect so that appropriate remedial action can be performed. The RGB signature itself is useful for flagging global defects, but the ADI also can detect "local" defects such as particles, scratches, comets, etc.

The ADI optical hardware primarily consists of a camera and a light source, such as a strobing Xenon or similar type lamp, for example. To ensure accurate inspection results, periodic maintenance of the ADI system must be performed. For example, as the light source degrades over time, the light source requires periodic calibration as well as replacement at the end of the light source's finite life. Such ADI preventive maintenance typically requires that the photolithography system be taken off line. For example, in order to calibrate the light source or determine whether the light source requires replacement, a technician must empty the photolithography system of production wafers and manually run calibration wafers on the system. This results in costly equipment down time while the preventive maintenance is completed.

Conventionally, preventive maintenance of the ADI system has been performed at arbitrary time intervals, such as four week intervals. However, such arbitrary intervals may not coincide with other preventive maintenance actions that require equipment down time, resulting in greater overall down time. Further, the light source may not require calibration at the scheduled interval, such as when the system has been used infrequently during the four week period, which also results in unnecessary tool down time. Still further, the light source may require calibration or replacement prior to the end of the four week period, resulting in inaccurate inspection results for production wafers inspected after the maintenance was actually required.

Finally, even where preventive maintenance of the ADI system is necessary, manual techniques for completing such maintenance are inherently time consuming and, as noted above, require a technician to take the photolithography system off line resulting in costly equipment down time.

SUMMARY OF THE INVENTION

Accordingly, one object of the present invention is to reduce or solve any of the above and/or other problems associated with scheduling or performance of ADI system preventive maintenance.

Another object of the invention is to provide a predictive model for automatically determining when preventive maintenance is required for an ADI system.

Still another object of the invention is to improve automation of ADI system preventive maintenance procedures.

These and/or other objects of the invention are provided by a method of determining preventive maintenance for an optical inspection system for inspecting photolithography processed substrates. The method includes measuring at least one operational characteristic of the optical inspection system and comparing a measurement result for said at least one operational characteristic with predetermined preventive maintenance criteria for the operational characteristic. Also included is determining a preventive maintenance requirement based on a comparison result of said comparing, and initiating a preventive maintenance action on said optical inspection system, said preventive maintenance action corresponding to said preventive maintenance requirement.

Another aspect of the invention includes a method of automatically performing preventive maintenance on an optical inspection system for inspecting photolithography processed substrates. The method includes determining a preventive maintenance action required for the optical inspection system and obtaining instructions for automatically performing said preventive maintenance action. The instructions are then executed on the optical monitoring system to perform said preventive maintenance action on the optical monitoring system.

Still another aspect of the invention includes an optical inspection system for inspecting photolithography processed substrates. The system includes a substrate holder configured to support a substrate to be inspected thereon, an inspection lamp configured to provide light incident on said substrate and a detector configured to detect an image of said substrate based on said light incident on the substrate. A controller is configured to determine a state of the substrate based on said image of the substrate, said controller further configured to execute instructions for automatically determining a preventive maintenance requirement or automatically performing a preventive maintenance action or both for said optical inspection system.

Still another aspect of the invention includes a method for retrofitting an after develop inspection (ADI) system to facilitate automated preventive maintenance on the ADI system. The method includes configuring a controller associated with the ADI with software required to automate determining preventive maintenance for the ADI or performing preventive maintenance for the ADI or both, and further making required hardware changes to the ADI for facilitate the automated preventive maintenance.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3 is a data structure showing various maintenance actions correlated with operational characteristics of the optical monitoring system according to an embodiment of the invention;

DESCRIPTION OF THE PREFERRED EMBODIMENTS

Figure 1:
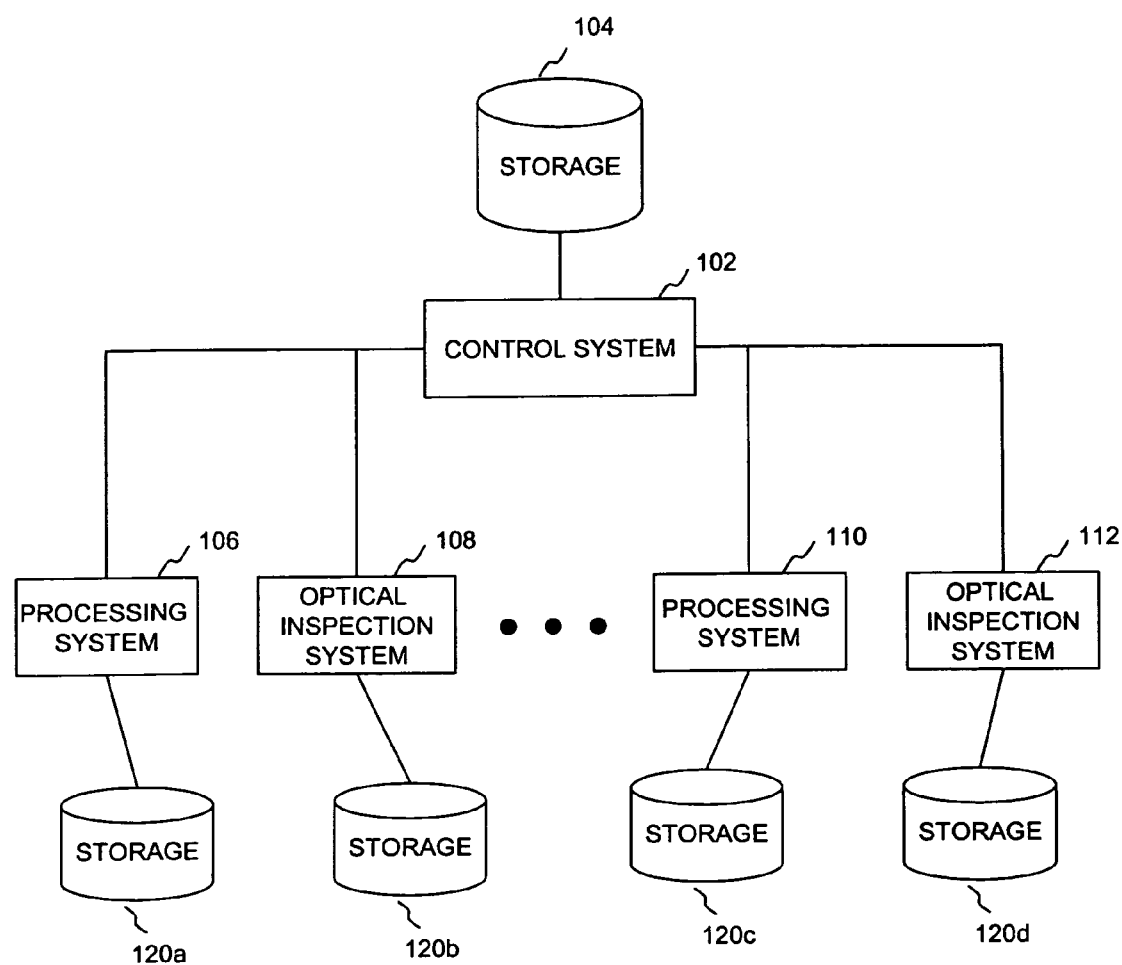
FIG. 1 is a schematic illustration of an exemplary photolithographic fabrication environment in which embodiments of the present invention have applicability.

Referring now to the drawings, wherein like reference numerals designate identical or corresponding parts throughout the several views, FIG. 1 depicts a schematic view of an automated photolithography system. While system of FIG. 1 is representative of a photolithography system, one of ordinary skill in the art would readily appreciate that such a photolithography system may be a subsystem of a larger semiconductor fabrication system having a host controller. The photolithography system of FIG. 1 includes a control system 102, processing systems 106, 110 and optical inspection systems (e.g. ADI tools) 108, 112. The processing systems are configured to perform various photolithography processes such as supplying a photoresist solution onto a semiconductor wafer, exposing the resist film to patterned light, and developing the pattern, and the optical inspections systems 108,112 inspect the processed wafers for defects. In the system of FIG. 1, control system 102 coordinates the operation of the different processing systems 106, 110 and inspection systems 108, 112. Furthermore, the control system 102 can control the automated transport of wafers between the different stations 106, 108, 110, 112, although a mechanism for transport is not shown in FIG. 1.

The control system 102 includes a microprocessor, memory, and a digital I/O port (potentially including D/A and/or A/D converters) capable of generating control voltages sufficient to communicate and activate inputs to, as well as monitor outputs from, each of the process stations 106, 110 and inspection stations 108, 112. The control system 102 communicates with the storage 104, processing systems, 106, 110, and optical inspection systems 108, 112 using any suitable protocol. A program stored in the memory (and obtained from storage 104, for example) is utilized to interact with the aforementioned processing and inspection systems according to a stored process or inspection recipe. One example of control system 102 is a DELL PRECISION WORKSTATION 640™, available from Dell Corporation, Austin, Tex. The control system may also be part of the fabrication system's host controller, which is a complex combination of hardware and software controls and communication protocols directed to overall control of the fabrication system.

The control system 102 may also be implemented as a general purpose computer, processor, digital signal processor, etc., which causes a processing system and/or optical inspection system to perform a portion or all of the processing steps of the invention in response to the control system 102 executing one or more sequences of one or more instructions contained in a computer readable medium. The computer readable medium or memory is configured to hold instructions programmed according to the teachings of the invention and can contain data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave, or any other medium from which a computer can read.

Control system 102 may be locally located relative to the processing and inspection systems in FIG. 1, or it may be remotely located relative to these systems. Thus, control system 102 can exchange data with process stations 106, 110 and inspection stations 108, 112 using at least one of a direct connection, an intranet, or the internet. Control system 102 may be coupled to an intranet at a customer site (i.e., a device maker, etc.), or coupled to an intranet at a vendor site (i.e., an equipment manufacturer). Furthermore, another computer (i.e., controller, server, etc.) can access control system 102 to exchange data via at least one of a direct connection, an intranet, or the internet.

When fabricating a wafer, as noted above, the control system 102 can run a process recipe and an inspection recipe, each of which specifies the steps and their order necessary to complete the fabrication of the wafer. These recipes can be stored at central storage 104 of the central control system 102, at any one of the storages 120a-120d locally connected to the stations 106, 110, 108, 112, stored in a remote storage location, or distributed among two or more of these storage locations. Further the recipes can be executed by the control system 102, individual controllers (not shown) associated with the stations 106, 110, 108, 112, or from a remote controller unit.

The storage units 104 and 120*a-d* contain files that include records containing information for controlling the process stations 106, 110 and inspection stations 108, 112, and also for facilitating preventive maintenance in accordance with embodiments of the present invention. This information can generally include preventive maintenance actions, operational characteristics of the optical inspection system, process recipes, inspection recipes, equipment history, etc. Such information may specifically include, for example, the number of strobes of an inspection light, the total voltage of an inspection light, stored inspection signatures of wafer maintenance action records, etc. Records in the storages 104 and 120*a-d* contain fields together with a set of operations for searching, sorting, recombining, and other database functions. The storages 104 and 120*a-d* may be implemented as two or more databases, if desired, including operations for searching, sorting, recombining, and other database functions.

Each optical inspection system 108, 112 includes an inspection light or lamp that illuminates a wafer being inspected. Each lamp has a number of settings that control the apparent brightness, or intensity, produced by the lamp. One way to measure the intensity of a lamp is through the use of a calibration wafer. According to this technique, an image of the calibration wafer is captured at each of the lamp settings. As understood by one of ordinary skill in this field, each such image can be characterized by an RGB signature that varies based on the lamp setting. In particular, the G (green) signature component of each image is used to characterize the lamp intensity at each setting.

During device fabrication, control system 102, or example, automates the process of inspection using inspection recipes that identify, at each inspection system 108, 112, the proper lamp setting to create a signature to compare with the golden wafer signature. Thus, the proper lamp setting during inspection is based on the intensity at which the golden wafer image was captured. More particularly, an inspection recipe specifies the desired lamp output level, such as the G signature value just described, and the control system 102, for example, automatically controls the inspection system 108, 112 lamp to select the appropriate lamp setting corresponding to the recipe's specified intensity.

Examples of a photolithography system of FIG. 1 are the CLEAN TRACK® systems produced by Tokyo Electron, Tokyo, Japan. However, it is to be understood that the system in FIG. 1 is for exemplary purposes only, as many variations of the specific hardware and software used to implement the present invention will be readily apparent to one having ordinary skill in the art. For example, the functionality of the control system 102 and one or more of the systems 106, 108, 110 and 112 may be combined in a single device. These and other implementations of a photolithography system are described in greater detail in one or more of U.S. Pat. No. 6,722,798 to Senba, et., and U.S. Pat. Nos. 6,811,962 and 6,991,385, both to Yoshihara, et al., each of which is incorporated herein by reference in their entirety. To implement these variations as well as other variations, a single computer may be programmed to perform the special purpose functions of two or more of any of the devices shown in FIG. 1. On the other hand, two or more programmed computers may be substituted for controllers at any one of the devices in FIG. 1. Principles and advantages of distributed processing, such as redundancy and replication, may also be implemented as desired to increase the robustness and performance of the system, for example.

Figure 2:
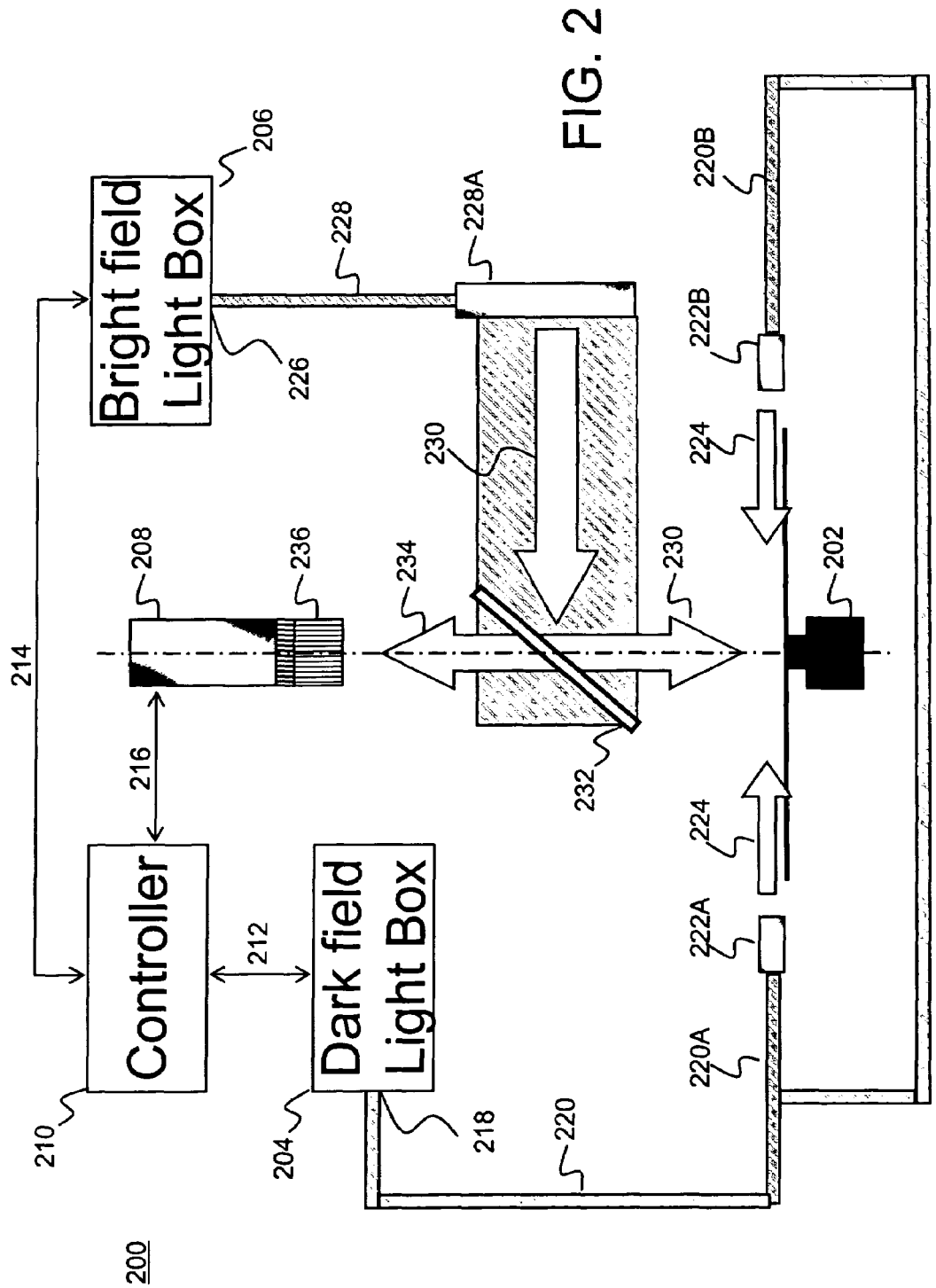
FIG. 2 is a schematic illustration of an optical inspection system in accordance with one embodiment of the invention.

FIG. 2. depicts an optical system 200 according to an embodiment of the invention. The system 200 includes a substrate holder 202, a dark field light box 204, a bright field light box 206, a detector 208 and a controller 210. The substrate holder 202 is configured to hold a substrate, such as a semiconductor wafer, to be inspected by the system 200. As will be understood by one of ordinary skill in the art, the substrate holder can be implemented to provide a variety of different functionalities such as clamping of the wafer, temperature control, etc. Further, the controller 210 can be part of the overall control system 102, or as a separate controller dedicated to the optical inspection system 200. As with the control system 102 explained above, the controller 210 may be implemented as a conventional computer or other more-specialized hardware platform. Whether stand alone or implemented with the overall control system 102, the controller 210 executes program instructions to cause the optical inspection system to perform all or a portion of the methods disclosed herein. As seen in FIG. 2, the controller 210 is configured to control the dark field light box 204, the bright field light box 206 and the detector 208 via signal cables 212, 214 and 216 respectively. The system of FIG. 2 may also include x, y, and theta stages (not shown) controlled by the controller 204 to move the wafer so that the detector can take multiple pictures to fully capture the wafer image.)

The dark field light box 204 outputs dark field light through a dark field light output 218 connected to a dark field fiber bundle 220. As seen in FIG. 2, the dark field fiber bundle 220 splits into bundles 220A and 220B, which feeds dark field illuminators 222A and 222B respectively. The illuminators 222A and 222B provide dark field light 224 from side positions of the substrate holder 202. In the embodiment of FIG. 2, the dark field light 224 is directed substantially parallel to the substrate holder 202 at side positions approximately 180 degrees apart from one another. However, dark field light 224 may be provided at an oblique/grazing incidence angle to the substrate holder 202, and at different positions. Further, the dark field lamp may not be used at all, as will be discussed below.

The bright field light box 206 outputs bright field light through a bright field light output 226 connected to a bright field fiber bundle 228. The bright field fiber bundle 228 feeds bright field illuminator 228A, which directs bright field light 230 to beam splitter 232. The beam splitter 232 directs at least a portion of the bright field light 230 toward a top surface of the substrate holder 202, and passes reflected light 234 from the surface of a substrate (held on the substrate holder 202) to the detector 208. As seen in FIG. 2, a lens 236 of the detector 238 collects the reflected light 234.

The detector 208 may be implemented as a CCD camera or other similar device. Further, as is well known to a skilled artisan, the detector 208 can include an adjustable gain level that affects the sensitivity of the detector 208. In a CCD for example, the gain level is used to adjust the count, or units, that is output upon the reception of a certain number of electrons at a pixel. The adjustable gain control is frequently implemented as external knobs or other similar mechanisms accessible from the exterior of the detector 208. More automated detectors or cameras, however, may provide a system interface that can be accessed via a display screen or interface port in order to adjust the gain level via software control. By adjusting the detector gain level, the red, green and blue values generated by the detector for a certain image are adjusted up or down. The detector gain control is advantageously adjustable for each of the red, green, and blue values of the detector 208. Typically, though, the green gain is not adjusted; instead the red and blue detector gain levels are adjusted as needed.

In operation of the inspection system 200, the controller 210 instructs the dark field light box 204 and bright field light box 206 when to flash and at what intensity. In one embodiment, the dark field lamp 204 may remain unused during the inspection, but serve as a back up lamp as will be further discussed below. The detector 208 then captures an image of a substrate on the substrate holder 202, and transmits this image to the controller 210 for further processing. U.S. Pat. App. No. 2005/0146716, to Dixon, et al. fully details inspection equipment in photolithographic environments and, more particularly, automated control of such equipment. Dixon et al. also teaches methods for calibrating ADI lamps. The entire content of Dixon et al. is incorporated herein by reference.

FIG. 3 depicts an exemplary data structure that may be used for implementing a system for facilitating preventive maintenance in accordance with an embodiment of the present invention. The data structure is depicted in a relational format, using a table, whereby information stored in one column (i.e., field) of a table is mapped or linked to information stored in the same row (i.e., record) across the other column(s) of the table. The data structure is used by the control system 102 and/or individual system controllers to facilitate preventive maintenance in accordance with embodiments of the present invention. According to one embodiment, the data structure shown in FIG. 3 is stored in a memory associated with the controller 210 so that an optical inspection system can determine preventive maintenance for the optical inspection system. However, the data structure may be stored in the storage 104 associated with control system 102, controller 210 and/or any other suitable storage device(s) or medium(s).

FIG. 3 is a maintenance action table 301 that includes a field 303 for storing maintenance actions and fields 305, 307 and 309 for storing predetermined maintenance criteria for different operational characteristics. The predetermined preventive maintenance criteria are a value of the operational characteristic that has been determined to correspond to some preventive maintenance action. Predetermined preventive maintenance criteria can be determined based on historical data, manufacturing specifications or any other information for a system or component that is relevant to a preventive maintenance action. In the embodiment of FIG. 3, field 305 includes a number of lamp strobes associated with each maintenance action in field 303. Similarly, field 307 includes a total voltage associated with each maintenance action in field 303, and field 309 includes inspection signature images associated with each maintenance action in field 303. The values in fields 305, 307 and 309 are predetermined preventive maintenance criteria. The strobe number, total voltage and signature operational characteristics will be further discussed below with respect to FIG. 4.

To illustrate the use of maintenance action table 301, FIG. 3 includes three exemplary entries. The first entry shows that field 303 may contain a maintenance action "lamp calibration," and in the same record, field 305 may contain the entry "100,000" the predetermined number of strobes that would initiate the lamp calibration action. Similarly, in the "lamp calibration record, field 307 includes the predetermined "voltage 1" and field 309 includes the predetermined "image 1" as a total voltage and inspection signature corresponding to the lamp calibration requirement. As seen in FIG. 3, the "lamp replacement" and "detector calibration" maintenance actions are included in respective records associated with a predetermined strobe number, total voltage and inspection signature. Thus, the maintenance action table 301 associates each of a number of maintenance actions with corresponding criteria of different operational characteristics for indicating when such action is required. The maintenance actions and operational characteristics shown in FIG. 3 are exemplary only.

Figure 4:
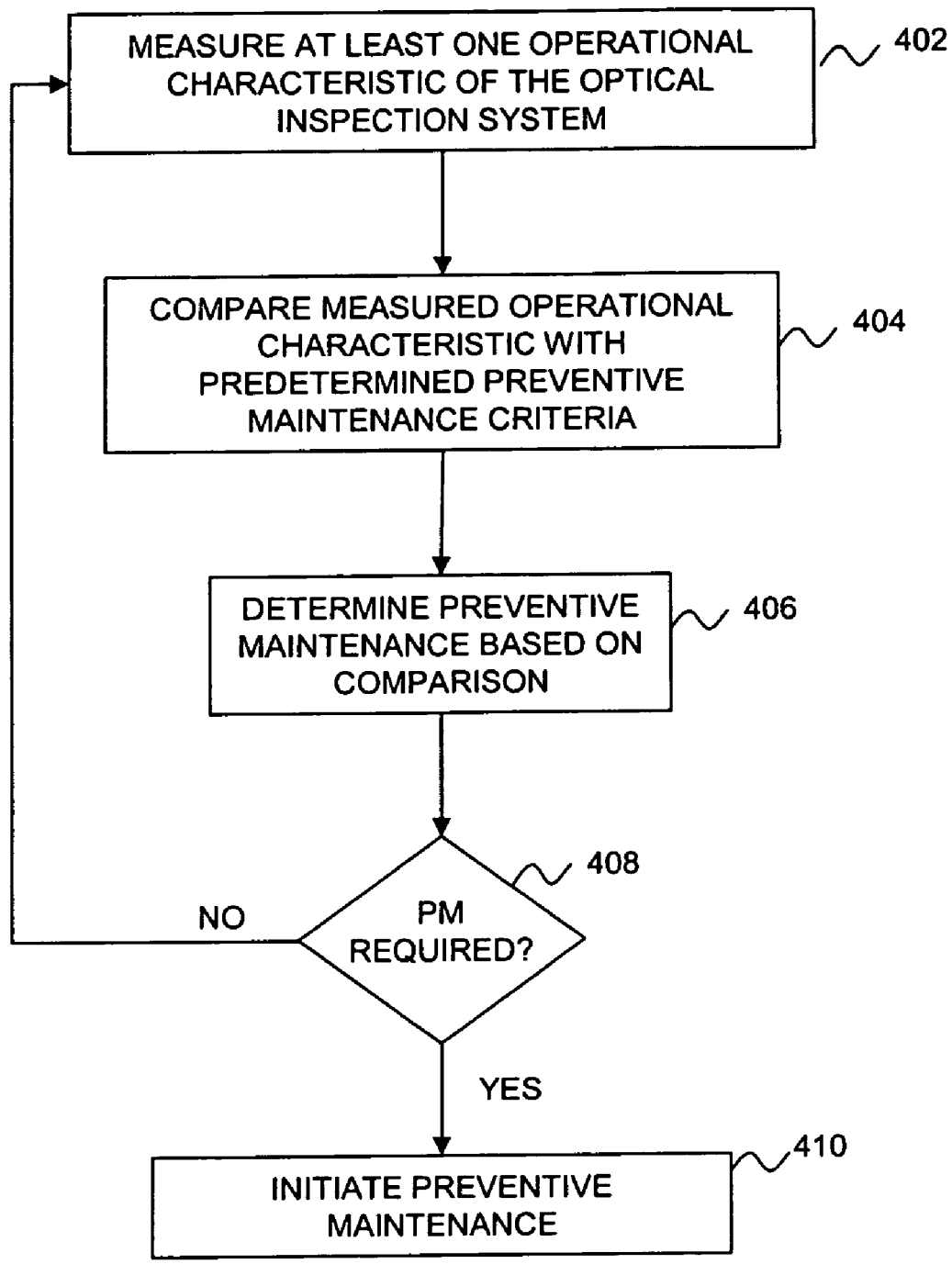
FIG. 4 illustrates a flowchart representing a method for determining preventive maintenance of an optical inspection system in accordance with an embodiment of the present invention.

FIG. 4 illustrates a flowchart representing a method for determining preventive maintenance of an optical inspection system in accordance with an embodiment of the present invention. As seen in this figure, the process begins with measuring at least one operational characteristic of the optical inspection system in step 402. As used herein, the term "operational characteristic" refers to at least one measurable characteristic of the optical inspection system other than elapsed time since a preventive maintenance action was taken on the system. For example, an operational characteristic can be the number of strobes of the inspection light, the total voltage applied to the inspection light, the number of detector operations, an inspection signature of the optical inspection system, a total number of wafers inspected by the system, or any other measurable characteristic of the optical inspection system. According to an exemplary embodiment of the invention, the control system 102, dark field light box 204, bright field light box 206 or controller 210, or all of these items may be programmed with special purpose software for measuring or tracking one or more operational characteristics of the optical inspection system.

Once the one or more operational characteristics are measured, the measured characteristic is compared with a predetermined preventive maintenance criteria correlated to the operational characteristic. For example, the maintenance action table of FIG. 3 shows 100,000 lamp strobes as the lamp calibration criteria, and 20,000,000 strobes as the lamp replacement criteria.

In step 406, preventive maintenance is determined based on the comparison in step 404. For example, the controller of the optical inspection system may compare a measured number of light strobes with the criteria in field 305 of FIG. 3 to determine if any maintenance action in field 303 of FIG. 3 is required. If it is determined that no preventive maintenance action is required, then the process returns back to step 402 as shown by the "NO" result of decision block 408. However, if it is determined that preventive maintenance is required, then the process continues to step 410 as shown by the "YES" result of decision block 408. In step 410, preventive maintenance determined in step 406 is initiated. Step 410 may be a simple indication to the system operator to manually perform the preventive maintenance, or a signal that triggers automatic performance of the preventive maintenance as will be further discussed below.

Thus, FIG. 4 shows a method for determining preventive maintenance in accordance with an embodiment of the invention. For example, the need for calibration and/or replacement of the inspection light may be determined based on the strobing frequency of the inspection lamp. As noted above, the optical inspection system can be configured to track the actual strobing history of its lamp. The simplest use of this data is to sum the actual number of strobes and compare this number to a quantity of strobes for a particular preventive maintenance action. A simple algorithm for achieving this may state: if # of strobes=x, then post message "PM is due" on display screen. Alternatively, the algorithm can include the capability to predict when upcoming preventive maintenance is due. For example, the algorithm may further calculate the average number of processed wafers per day based on historical data, and predict when the next preventive maintenance is due assuming the average number of processed wafers in future days. The predicted date may be periodically updated (based on a newly calculated average use) and provided to the system operator at predetermined intervals.

One example method for predicting preventive maintenance based on average daily strobe volume can first define necessary data parameters as follows:

S=measured # of lamp strobes since last preventive maintenance (PM);
X=# of lamp strobes until next PM is due;
D=measured # of days elapsed since last PM;
W=# of days warning required before next PM is due;
A=average # of strobes/day; and
Z=predicted # of days until PM is due.

Once the parameters are defined and the S and D values are measured by the photolithography and/or optical inspection system, the average daily strobe history can be calculated as, $$A=S/D,$$

and the predicted number of days until the next preventive maintenance can be calculated as, $$Z=X/A.$$

In operation, the predicted number of days until the next preventive maintenance is compared to the amount of advance warning the system operator has specified, and the operator is notified as follows, If $Z \leq W$, then post message "PM is due in", Z, "days."

While the above example provides a useful prediction and/or determination of when preventive maintenance is due, simply counting the number of lamp strobes may not provide an accurate metric for determining preventive maintenance in all circumstances. Each optical inspection recipe (e.g. ADI inspection recipe) requires a particular lamp intensity, and one inspection system can run a variety of recipes. For example, one optical inspection system might run predominantly front end of line product which tends to require higher lamp intensities, while another optical inspection system might run predominantly back end of line product which requires lower lamp intensities. Further, a lamp that consistently strobes at 10% intensity will have a longer life than one that consistently strobes at 90% intensity, for example. As a result, two inspection systems each having 20 million lamp strobes can actually be in different states and have far different requirements for the next preventive maintenance action.

Thus, according to one embodiment of the invention, the preventive maintenance is determined based on an "equivalent number of lamp strobes" correlated to the total applied voltage or intensity of the lamp. Specifically, when summing the lamp strobes to determine the number of strobes since the last preventive maintenance (S parameter noted above), the number of strobes in a particular wafer batch can be scaled by a strobe number scaling factor as follows:

$$Sbatch=Sactual*(Vactual/Vmaximum)$$

$$Sbatch=Sactual*(Iactual/Imaximum),$$

where, Sbatch is the scaled strobe number for a batch, Sactual is the actual counted number of strobes, Vactual/Vmaximum is the voltage scaling factor, and Iactual/Imaximum is the intensity scaling factor. Further, Vmaximum and Imaximum are the maximum voltage and intensity the lamp can tolerate.

In the above equations for Sbatch, the strobe number scaling terms (Vactual/Vmaximum) and (Iactual/Imaximum) are formed under the assumption that the lamp life depends linearly on the applied voltage (or intensity). However, the scaling terms can take on other functional forms, such as power function, or an exponential function as follows:

$$Sbatch=Sactual*[A*(Vactual/Vmaximum)\hat{\ }b+C]$$

$$Sbatch=Sactual*[A*e\hat{\ }(((Vactual/Vmaximum)*b)+C)+D],$$

where A, b, C, and D are constants. Another possibility is the use of a polynomial, of any power n, of the term (Vactual/Vmaximum) as follows:

$$Sbatch=Sactual*[A1*(Vactual/Vmaximum)\hat{\ }n+$$
$$A2*(Vactual/Vmaximum)\hat{\ }(n-1)+\ldots+An*(Vactual/Vmaximum)+$$
$$An+1],$$

where Ai, i=1 . . . n+1 are constants.

As would be understood by one of ordinary skill in the art, Sbatch may be determined based on any one or more of the above scaling functions, or additional scaling functions that can provide an accurate prediction of lamp lifetime and/or calibration requirements. For example, if the vendor provided a lamp life vs. intensity curve, or a lamp life vs. voltage curve, then this curve can be used to determine the number of remaining strobes until preventive maintenance is required. Specifically, the curve can be stored in a software lookup table in the storage system 102 and used to scale the actual number of strobes in a batch. Alternatively, this curve can be converted into one of the forms discussed above (power, exponential, polynomial, etc.). Once the Sbatch is determined, the total number of "equivalent" strobes would then be the sum of all Sbatch, over all batches run in the tool since the preventive maintenance was performed, as follows:

$$Sequivalent=sum(Sbatch).$$

Still another mechanism for determining preventive maintenance is the optical inspection itself. For example, when an ADI bulb surpasses its lifetime, the strobing becomes erratic and displays a particular signature indicative of a bulb that requires replacement, and in some instances can identify that calibration is required. For example, there is a definite drop off in intensity of certain strobes, which creates a darker rectangular strobing signature in the wafer image when the bulb has exceeded its life. The optical inspection system software can be modified to recognize this signature in wafer images, and then initiate a preventive maintenance action. Although using this signature recognizes the need for a bulb change after the lamp has started to fail, this could still be useful to some operators that want to maximize the lamp life of a high cost inspection bulb, at the risk of improper inspection of wafers.

Figure 5:
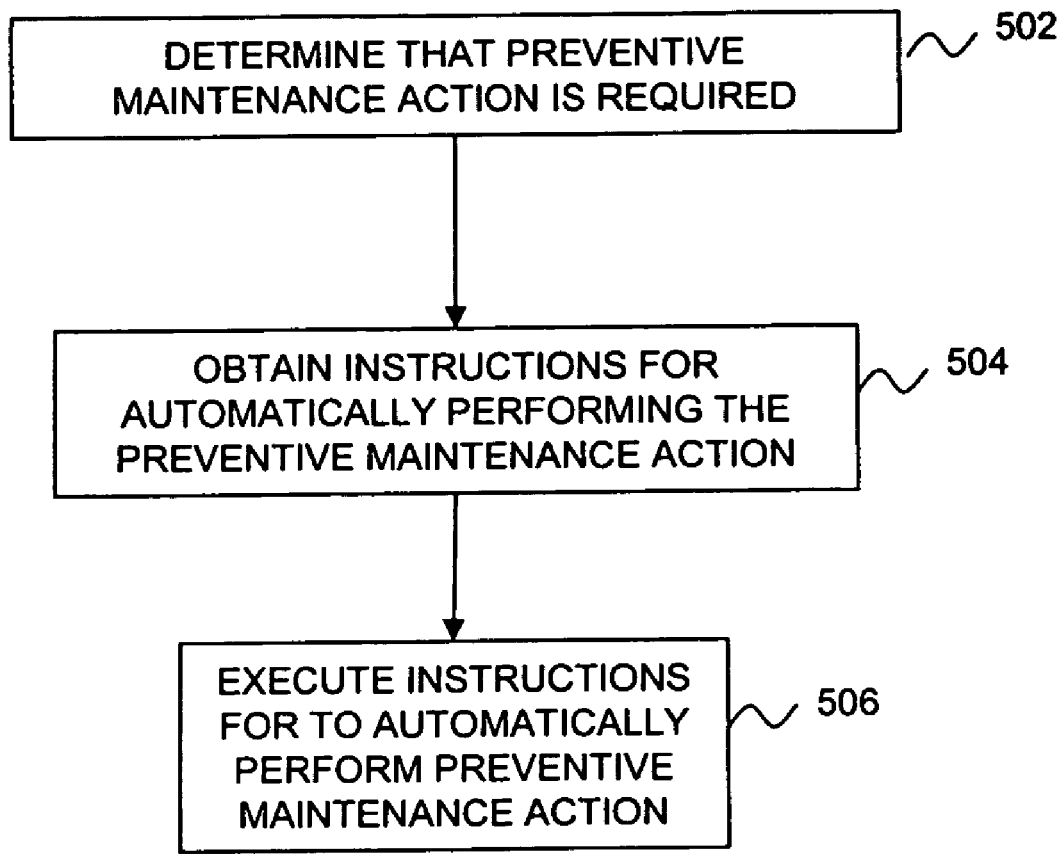
FIG. 5 illustrates a flowchart representing a method for automatically performing a preventive maintenance action on an optical inspection system in accordance with an embodiment of the present invention.

As discussed in the Background section above, preventive maintenance on optical inspection systems such as ADI systems has conventionally been manually performed, which is inefficient and results in equipment down time. FIG. 5 illustrates a flowchart representing a method for automatically performing a preventive maintenance action on an optical inspection system in accordance with an embodiment of the present invention. As seen in this figure, the method begins in step 502 with determining that a preventive maintenance action is required. This step is preferably done automatically by the optical inspection system using any one of the techniques discussed above, for example. However, the determination may be done manually by the operator, or based on an arbitrary time interval. While the arbitrary time interval may result in preventive maintenance performed before it is actually due, this may not result in system down time because the automation of the preventive maintenance action can allow the maintenance action to be done during system operation on production wafers (i.e. between wafers, wafer cassettes, or wafer batches).

In step 504, instructions for automatically performing the preventive maintenance action are obtained by the optical inspection system. In one embodiment, the instructions are retrieved from a memory within the optical inspection system itself. However, the instructions may be obtained from a remote computer such as the control system 102 and storage 104. In one embodiment, the instructions include a calibration recipe used to calibrate the inspection light and/or detector. Alternatively, the instructions include control functions for replacing or exchanging the inspection light, as will be further discussed below. In step 506, the instructions obtained in step 504 are executed to automatically perform the preventive maintenance on the optical inspection system. Thus, the instructions may cause calibration of the inspection light or detector, or replacement of the inspection light, for example.

Thus, FIG. 4 illustrates a method for automatically performing preventive maintenance on an optical inspection system. In one embodiment, the preventive maintenance can be automatically performed during operation of the optical inspection system, such that production continues. However, the preventive maintenance can also be efficiently performed between production runs on the system. In one exemplary embodiment, an optical inspection system such as an ADI determines that calibration of the inspection light is required, and sends a calibration request to a remote controller dedicated to automated preventive maintenance. The dedicated controller then retrieves a calibration cassette having calibration wafers therein. As would be appreciated by one of ordinary skill in the art, such cassettes can be stored by the customer,called from storage and sent to an inspection tool through a fab controller The dedicated controller also sends calibration recipes to the photolithography/ADI system. The ADI software then runs the calibration recipes to generate a new lamp calibration file and optionally to check/adjust camera gain settings of the inspection system.

Figure 6:
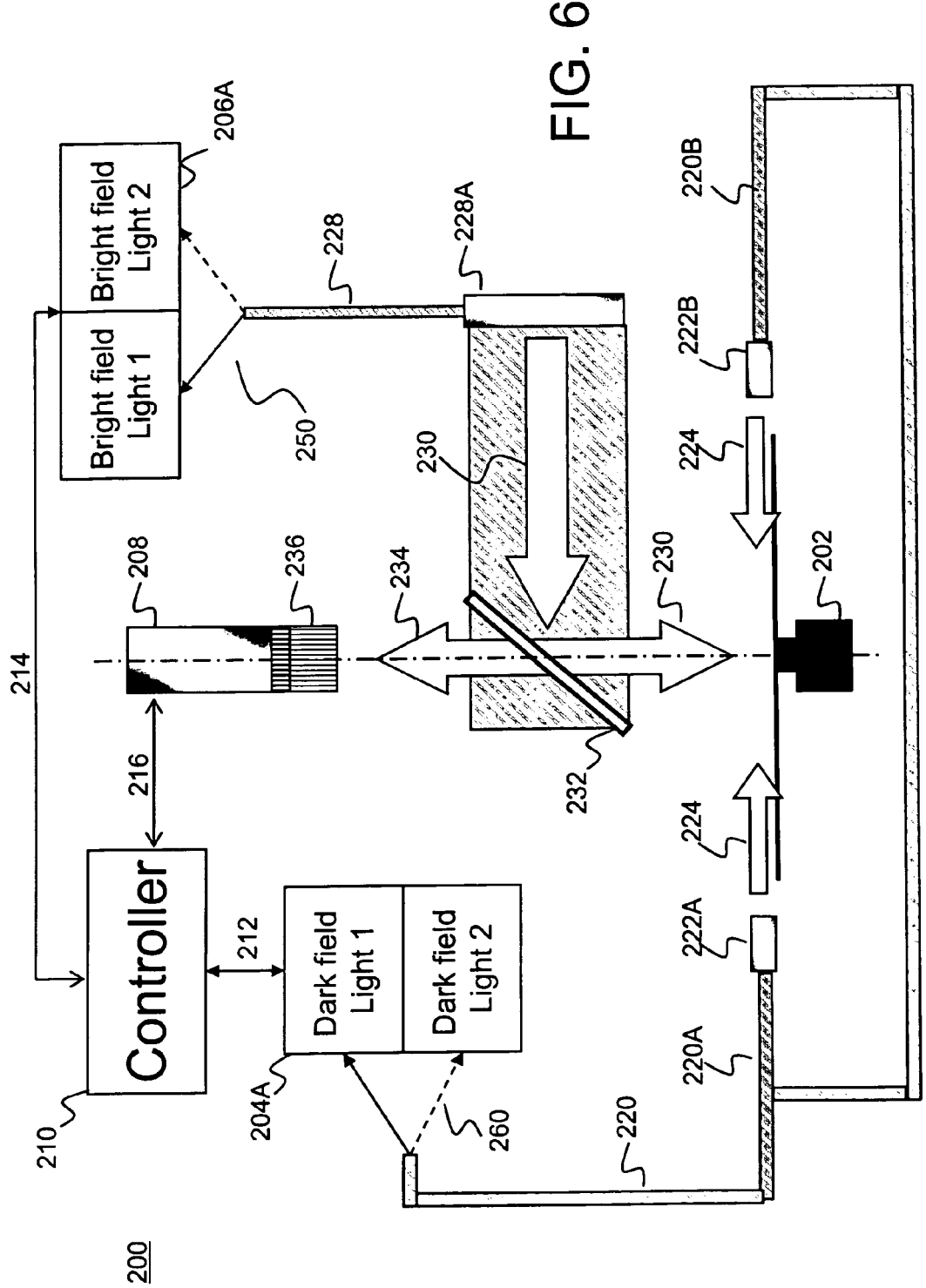
FIG. 6 shows a schematic illustration of hardware changes that may be implemented on a an optical inspection system in accordance with an embodiment of the invention.
Figure 7:
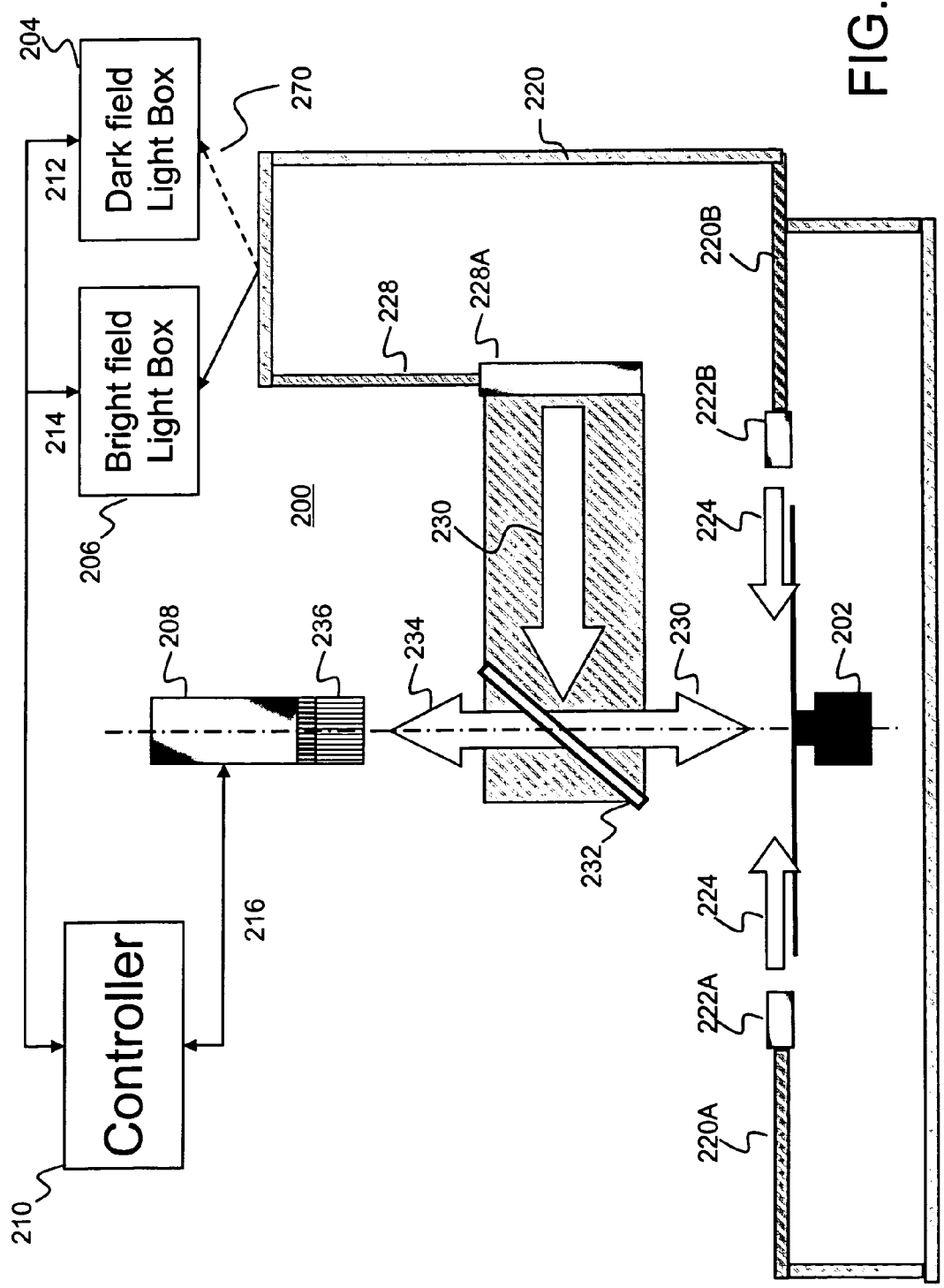
FIG. 7 shows a schematic illustration of hardware changes that may be implemented on an optical inspection system in accordance with another embodiment of the invention.

The automated calibration example provided above may be implemented with software changes to the photolithography system and/or optical inspection system, but would require little or no hardware modifications. For automating other preventive maintenance actions, however, hardware modifications may be required. For example, FIGS. 6 and 7 are schematic illustrations of hardware changes that can be made to the optical inspection system of FIG. 2 in order to provide an automated solution for replacing or exchanging the inspection lamp of the system. In these figures, discussion of the items described with respect to FIG. 2 are not repeated.

As seen in FIG. 6, one modification would be to provide a dark field light box 204A and a bright field light box 206A, each having 2 lights. Switch 260 switches connection of the fiber bundle 220 between the first and second dark field lights, and switch 250 similarly switches the fiber bundle 228 between the first and second bright field lights. As would be understood by one of ordinary skill in the art, the switches 250 and 260 can be implemented in a variety of ways. For example, the switches 250, 260 can be implemented as an automated mechanism for physically switching the fiber bundles between light outputs, or as a optical switch for switching light paths between the first and second lights. Further, the light boxes 204A and 206A could each include two separate lamp control circuits that could be switched on/off to automatically change the light path between fiber bundles, and the signal path between signal lines. Alternatively, bifurcated fiber bundles leading to both dark field lamps of lamp box 204A and/or both bright field lamps of lamp box 206A may be used, without the need for switches 260 and/or 250. In one embodiment of a bifurcated fiber bundle, the bundle of optical fibers is split into two bundles, as is the case with dark field fiber bundle 220, which is bifurcated to simultaneously supply light to both dark field illuminators 222A and 222B. Other configurations may also be used.

FIG. 7. illustrates an alternative hardware modification for automatic inspection light replacement according to an embodiment. Although optical inspection systems generally include dark field and bright field light sources as discussed with respect to FIG. 2, the dark field light is often not used, and is left uncalibrated. Thus, as seen in FIG. 7, the dark field light box 204 can be used for redundancy by incorporating switch 270 into the system. Specifically, the switch 270 can switch light from the bright field box 206 to the dark field box 204 when the bright field light requires replacement. As noted above, one of ordinary skill in the art could implement the switch 270 in a variety of ways, such as by mechanical or optical switching. Further, signal cables 212 and 214 can be exchanged to provide proper signaling of the lamp box, and such exchange can be automated by a signal switch. Still another solution would be to maintain fiber bundle and signal connections to the dark field and bright field light boxes, but mechanically swap positions of the illuminators. For example, the illuminators 224 and 228 could be mounted on movable arms so that the normal incidence bright field illuminator can be swung into the grazing illumination position, and vice versa. Alternatively, as discussed with respect to FIG. 6, fiber bundle bifurcations may be used to permanently connect all lamps and illuminators, without the need for switches. In the case of the embodiment of FIG. 7, fiber bundle 220 would be bifurcated to connect to both the bright field light box 206 and dark field light box 204 (e.g. in addition to already being bifurcated on the other end to supply the bright field illuminator 228A, and dark field illuminators 222A and 222B).

Thus, FIGS. 6 and 7 illustrate example hardware modifications for providing redundant light sources that can allow a backup light to be used in the optical inspection system so that wafer inspections can continue until a convenient time for replacing the degraded light source. Preferably, the degraded light source can be replaced while inspection of production wafers continues with the backup bulb. Various techniques can be used to implement this concept, such as providing unimpeded external access to light boxes 204 and 206 while the tool is running.

As would be understood by one of ordinary skill in the art, all aspects of the present invention may be, individually or in combination, implemented in a retrofit procedure to an existing optical inspection system. For example, a conventional photolithography system and/or optical inspection system can be modified to store information, including data structures and program instructions, for determining and/or performing preventive maintenance. Hardware changes such as those described in FIGS. 6 and 7 may also be provided through a retrofit procedure. For example, the dark field fiber bundle 220 and the bright field fiber bundle 228 in FIG. 2 may be replaced by a bifurcated fiber bundle discussed above. Other system modifications necessary to implement the present invention would be readily apparent to one of ordinary skill in the art.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of determining preventive maintenance for an optical inspection system for inspecting photolithography processed substrates, the method comprising:
    measuring at least one operational characteristic of the optical inspection system, the optical inspection system configured to capture images of the photolithography processed substrates after completion of photolithography;
    comparing a measurement result for said at least one operational characteristic with predetermined preventive maintenance criteria for the operational characteristic;
    determining a preventive maintenance requirement based on a comparison result of said comparing; and
    initiating a preventive maintenance action on said optical inspection system, said preventive maintenance action corresponding to said preventive maintenance requirement.

2. The method of claim 1, wherein said measuring comprises measuring an actual number of strobes of an inspection light of the optical inspection system.

3. The method of claim 1, wherein said measuring comprises measuring a characteristic of a detector of the optical inspection system.

4. The method of claim 1, wherein said measuring comprises measuring an inspection signature resulting from a substrate inspection performed by the inspection system.

5. The method of claim 1, wherein said determining comprises determining an inspection light calibration requirement or an inspection light replacement requirement or both for said optical inspection system.

6. The method of claim 1, wherein said initiating comprises notifying an operator of said optical inspection system that the preventive maintenance action on is required for said optical inspection system.

7. The method of claim 1, wherein:
    said determining comprises predicting a preventive maintenance requirement based on said comparison result of said comparing, and
    said initiating comprises notifying an operator of the optical inspection system of the predicted preventive maintenance requirement.

8. The method of claim 2, wherein said measuring further comprises determining an equivalent number of strobes by scaling the actual number of strobes according to a scaling function.

9. The method of claim 2, wherein:
    said comparing comprises comparing the measured number of actual strobes with a predetermined number of strobes representing a state of an inspection light of the optical inspection system, and
    said determining comprises determining whether inspection light calibration or inspection light replacement is required for the inspection light based on said comparing.

10. The method of claim 4, wherein:
    said comparing comprises comparing the measured inspection signature with a predetermined inspection signature representing a state of an inspection light of the optical inspection system, and
    said determining comprises determining whether inspection light calibration or inspection light replacement is required for the inspection light based on said comparing.

11. The method of claim 8, wherein said determining comprises scaling the actual number of strobes according to a voltage scaling function or an intensity scaling function or both.

12. The method of claim 8, wherein said determining comprises scaling the actual number of strobes according to a voltage to lifetime curve or an intensity to lifetime curve or both.

\* \* \* \* \*